US007074555B2

(12) United States Patent
Esty et al.

(10) Patent No.: US 7,074,555 B2
(45) Date of Patent: Jul. 11, 2006

(54) DETECTION OF WEST NILE VIRUS

(75) Inventors: Katherine Jean Esty, Westbrook, ME (US); Ramaswamy Chandrashekar, Scarborough, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 10/834,424

(22) Filed: Apr. 28, 2004

(65) Prior Publication Data

US 2005/0244814 A1 Nov. 3, 2005

(51) Int. Cl.
*C12Q 1/70* (2006.01)
(52) U.S. Cl. ........................... 435/5; 435/69.7; 530/350
(58) Field of Classification Search ............. 424/218.1, 424/186.1, 192.1; 435/5, 69.7; 530/350
See application file for complete search history.

(56) References Cited

U.S. PATENT DOCUMENTS

| | | | |
|---|---|---|---|
| 2003/0022949 A1 | 1/2003 | Chang | |
| 2003/0091595 A1 | 5/2003 | Chu | |
| 2003/0104008 A1 | 6/2003 | Loosmore et al. | |
| 2003/0148261 A1 | 8/2003 | Fikrig et al. | |
| 2003/0149252 A1 | 8/2003 | Gourdin et al. | |
| 2004/0037848 A1* | 2/2004 | Audonnet et al. | 424/199.1 |
| 2004/0197769 A1* | 10/2004 | Wong et al. | 435/5 |

FOREIGN PATENT DOCUMENTS

| | | |
|---|---|---|
| WO | 0075665 | 12/2000 |
| WO | 02 072036 | 9/2002 |
| WO | 02 081754 | 10/2002 |
| WO | 0440263 | 5/2004 |
| WO | WO 2004040263 A2 * | 5/2004 |
| WO | 0524427 | 3/2005 |

OTHER PUBLICATIONS

Beasley DW, et al., Identification of neutralizing epitopes within structural domain III of the West Nile virus envelope protein. J Virol. Dec. 2002;76(24):13097-100.*
Davis, B.S. et al., West Nile virus recombinant DNA vaccine protects mouse and horse from virus challenge and expresses in vitro a noninfectious recombinant antigen that can be used in enzyme-linked immunosorbent assays. J Virol. May 2001;75(9):4040-7.*
Seppanen, H., Development of a highly specific and sensitive rubella immunoglobulin M antibody capture enzyme immunoassay that uses enzyme-labeled antigen (Apr., 1990) Journal of Clinical Microbiology, 28(4):719-723.*
Wang T, et al., Immunization of mice against West Nile virus with recombinant envelope protein. J Immunol. Nov. 1, 2001;167(9):5273-7.*

Wang T, et al., West Nile virus envelope protein: role in diagnosis and immunity. (Dec. 2001) Ann N Y Acad Sci.; 951:325-7.*
Wang T, et al., A recombinant envelope protein-based enzyme-linked immunosorbent assay for West Nile virus serodiagnosis. (Summer 2002 Summer) Vector Borne Zoonotic Dis.;2(2):105-9.*
Wong, S.J. et al., Detection of human anti-flavivirus antibodies with a west nile virus recombinant antigen microsphere immunoassay (Jan. 2004) J Clin Microbiol.; 42(1):65-72.*
Ebel, G., et al., *Detection by Enzyme-Linked Immunosorbent Assay of Antibodies to West Nile Virus in Birds*, Emerging Infectious Diseases 8(9):979-981 (2002).
Martin, D., et al., *Standarization of Immunoglobulin M Capture Enzyme-Linked Immunosorbent Assays for Routine Diagnosis of Arboviral Infections*, Journal of Clinical Microbiology 38(5):1823-1826 (2000).
Martin, D., et al., *Use of Immunoglobulin M Cross-Reactions in Differential Diagnosis of Human Flaviviral Encephalitis Infections in the United States*, Clinical and Diagnostic Laboratory Immunology 9(3):544-549 (2002).
Cantile, C., et al., *Clinical and neuropathological features of West Nile Virusequine encephalomyelitis in Italy*, Equine Vet. J, 32(1):31-35 (2000).
Feinstein, S., et al., *Determination of Human IgG and IgM Class Antibodies to West Nile Virus by Enzyme Linked Immunosorbent Assay (Elisa)*, J. Med. Virol. 17(1):63-72 (1985).
Lanciotti, R., et al., *Origin of the West Nile Virus Responsible for an Outbreak of Encephalitis in the Northeastern United States*, Science 286 (17):2333-2337 (1999).
Hall, R., et al., *Epitope Analysis of teh Envelope and Non-Structural Glycoproteins of Murray Valley Encephalitis Virus*, Journal of General Virology 71:2923-2930 (1990).
Hall, R., et a.l, *Monoclonal Antibodies to Kunjin and Kokobera Viruses*, Immunology and Cell Biology 69:47-49 (1991).
Hall, R., et a.l, *Immunodominant Epitopes on the NS1 Protein of MVE and KUN Viruses serve as targets for a blocking ELISA to Detect Virus-Specific Antibodies in Sentinel Animal Serum*, Journal of Virological Methods 51:201-210 (1995).

(Continued)

*Primary Examiner*—Jeffrey Stucker
*Assistant Examiner*—Michael M. McGaw
(74) *Attorney, Agent, or Firm*—McDonnell Boehnen Hulbert & Berghoff LLP

(57) ABSTRACT

A method and device for detecting a West Nile Virus (WNV) infection including contacting a biological sample from a subject with an anti-IgM antibody and a recombinant WNV E polypeptide and detecting whether the polypeptide substantially binds to an antibody in the sample. The invention also includes a method and device for determining whether an animal is infected with West Nile Virus (WNV), or is either not infected or is vaccinated with a WNV vaccine.

16 Claims, No Drawings

OTHER PUBLICATIONS

Blitvich, et al., *Serologic Evidence of West Nile Virus Infection in Horses, Coahuila State, Mexico*, Emerging Infectious Diseases 9(7):853-856 (2003).

Blitvich, et al., *Epitope-Blocking Enzyme-Linked Immunosorbent Assays for the Detection of Serum Antibodies to West Nile Virus in Multiple Avian Species*, Journal of Clinical Microbiology 41(3):1041-1047 (2003).

Yamshchikov, et al., *An Infectious Clone of the West Nile Flavivirus*, Virology 281:294-304(2001).

Hubálek, et al., *West Nile Fever—a Reemerging Mosquito-Borne Viral Disease in Europe*, Emerging Infectious Diseases 5:643-650 (1999).

Wong, Susan J., et al., *Immunoassay Targeting Nonstructural Protein 5 to Differentiate West Nile Virus Infection from Dengue and St. Louis Encephalitis Virus Infections and from Flavivirus Vaccination*, Journal of Clinical Microbiology 41(9):4217-4223 (2003).

Jozan, Martine, et al., *Detection of West Nile Virus Infection in Birds in the United States by Blocking ELISA and Immunohistochemistry*, Vector-Borne and Zoonotic Diseases 3(3):99-110 (2003).

Shi, Pei-Yong, et al., "*Serologic Diagnosis of West Nile Virus Infection*", Expert Review of Molecular Diagnostics, 2003, vol. 3(6), pp. 733-741.

Davis, B., et al. "*West Nile Virus Recombinant DNA Vaccine Protects Mouse and Horse from Virus Challenge and Expresses in Vitro a Noninfectious Recombinant Antigen that can be Used in Enzyme-Linked Immunosorbent Assays*", Journal of Virology, 2001, vol. 75(9), pp. 4040-4047.

Porter, Michael B., et al., "*Immunoglobulin M-Capture Enzyme-Linked Immunosorbent Assay Testing of Cerebrospinal Fluid and Serum from Horses Exposed to West Nile Virus by Vaccination or Natural Infection*", J. Vet. Intern Med., 2004, vol. 18, pp. 866-870.

\* cited by examiner

DETECTION OF WEST NILE VIRUS

BACKGROUND OF THE INVENTION

1. Field of the Invention

The invention is related to the detection of West Nile Virus (WNV) infections in animals.

2. Description of Related Art

Known as a Flavivirus, the West Nile virus was first identified in 1937 in Africa and first found in North America in 1999. Migratory birds are considered the primary means whereby infection is spread within and between countries. The virus is transmitted by mosquitoes that have acquired infection by feeding on viremic birds. The virus is then amplified during periods of adult mosquito blood-feeding. Infected mosquitoes then transmit the virus to humans and animals upon feeding thereon.

West Nile virus is the causative agent for West Nile Virus disease, particularly West Nile encephalitis, predominately in humans, other mammals and birds. The chief concern in both the United States and foreign countries is the lack of effective treatment for West Nile virus disease. Anti-inflammatory drugs are used to combat swelling of central nervous system tissues, but beyond that no medical intervention is currently available.

The West Nile fever virus also affects horses, particularly in North America and Europe (Cantile C. et al., Equine Vet. J., 2000, 32 (1), 31–35). These horses reveal signs of ataxia, weakness of the rear limbs, paresis evolving towards tetraplegia and death. Horses and camels are the main animals manifesting clinical signs in the form of encephalitis.

The virions of the West Nile fever virus are spherical particles with a diameter of 50 nm constituted by a lipoproteic envelope surrounding an icosahedric nucleocapsid containing a positive polarity, single-strand RNA. A single open reading frame (ORF) encodes all the viral proteins in the form of a polyprotein. The cleaving and maturation of this polyprotein leads to the production of several different viral proteins. The structural proteins are encoded by the 5' part of the genome and correspond to the nucleocapsid designated C (14 kDa), the envelope glycoprotein designated E (50 kDa), the pre-membrane protein designated prM (23 kDa), and the membrane protein designated M (7 kDa). The non-structural proteins are encoded by the 3' part of the genome and correspond to the proteins NS1 (40 kDa), NS2A (19 kDa), NS2B (14 kDa), NS3 (74 kDa), NS4A (15 kDa), NS4B (29 kDa), and NS5 (97 kDa).

Vaccines for WNV are described, for example, in U.S. Patent Publication Nos. 2003/0148261A1, 2003/0104008A1 and 2003/0091595A1, each of which is incorporated herein by reference in its entirety. Publication No. 2003/0091595 describes a WNV vaccine that includes an inactivated whole or subunit WNV. Publication No. 2003/0104008 discloses a vector, such as recombinant avipox virus, containing and expressing exogenous polynucleotide(s) from WNV to induce an immune response against WNV. These recombinant WNV vaccines include a vector containing a polynucleotide having single encoding frame corresponding to, for example, prM-E, M-E and prM-M-E. The vector may include several separate polynucleotides encoding the different proteins (e.g. prM and/or M and E). The vector can also include polynucleotides corresponding to more than one WN virus strain, for example, two or more polynucleotides encoding E or prM-M-E of different strains. Furthermore, the vector can include one or more nucleotide sequences encoding immunogens of other pathogenic agents and/or cytokins. Publication No. 2003/0148261 describes various WNV polypeptides and immunogenic fragments for use in WNV vaccines. These vaccines are produced recombinantly using various vectors encoding WNV polypeptides and the vectors are expressed by a variety of host cells.

Various method for detecting WNV are known. E. g., Feinstein, S, et al., *Determination of human IgG and IgM class antibodies to West Nile virus by enzyme linked immunosorbent assay* (ELISA), J Med Virol. 1985; 17(1):63–72; Martin, D A, et al., *Standardization of Immunoglobulin M Capture Enzyme-Linked Immunosorbent Assays for Routine Diagnosis of Arboviral Infections*, J. Clin. Micro., 2000; 38(5): 1823–1826. Martin et al describe the currently accepted CDC method, known generally as a MAC-ELISA, for detecting IgM produced by an animal in response to an exposure to a WNV antigen. Generally, this method involves contacting goat anti-IgM coated plates with a sample and incubating the plate overnight. Following the incubation, the plate, having bound IgM from the sample, is then contacted with WNV antigen from virus infected suckling mouse brain or unpurified C6/36 cell culture supernates. This is followed by the addition of flavivirus group reactive monoclonal antibody conjugated to HRP and a further incubation. Bound conjugate is detecting by adding TMB substrate and $A_{450}$ is measured.

The CDC MAC-ELISA takes between 24 and 72 hours to complete, with at least one overnight incubation. While this assay can effectively detect exposure to a WNV antigen, the assay cannot detect whether a positive result is due to a natural WNV infection or vaccination of the animal. Therefore, asymptomatic animals that have an unknown vaccination status testing positive for the MAC-ELISA may incorrectly be diagnosed as positive for WNV infection when, in fact, the animal has developed antibodies to WNV as a result of vaccination. Thus, what is needed is a rapid method of detecting exposure to a WNV antigen. Also, a method is needed that can distinguish between animals that have been naturally infected with WNV from animals that have been vaccinated.

SUMMARY OF THE INVENTION

In one aspect, the invention is directed to a method for detecting antibodies to West Nile Virus (WNV) in a biological sample. The method includes contacting the biological sample with an immobilized anti-IgM antibody and a labeled WNV E polypeptide, and detecting whether the polypeptide substantially binds to an antibody in the sample. The polypeptide may be synthetic or isolated, and it may be a recombinant polypeptide. The biological sample may be obtained from a horse and the anti-IgM antibody may be anti-horse IgM.

In another aspect, the invention also provides for optimizing the method so that the method will detect WNV antibodies in a sample from animals that have been naturally infected but the method will not detect antibodies in a sample from animals that have been vaccinated. The method may be optimized by diluting the sample and/or adjusting the concentration of the polypeptide.

The method may include incubating the sample with a solid phase having an immobilized anti-IgM antibody simultaneously with the polypeptide or incubating the sample with a solid phase having an immobilized anti-IgM antibody prior to contacting the sample with the polypeptide.

In a further aspect, the invention is directed to a device and a kit for detecting antibodies to West Nile Virus (WNV) in a biological sample.

DETAILED DESCRIPTION

Before describing the present invention in detail, a number of terms will be defined. It is to be understood that the terminology used herein is for the purpose of describing particular embodiments only, and is not intended to be limiting. As used herein, the singular forms "a," "an," and "the" include plural referents unless the context clearly dictates otherwise.

As used herein, the term "polypeptide" refers to a compound of a single chain or a complex of two or more chains of amino acid residues linked by peptide bonds. The chain(s) may be of any length and may consist of a fusion protein. Although "protein" is often used in reference to relatively large polypeptides, and "peptide" is often used in reference to small polypeptides, usage of these terms in the art overlaps and varies. The term "polypeptide" as used herein thus refers interchangeably to peptides, polypeptides, or fusion proteins unless otherwise noted. The term "amino acid" refers to a monomeric unit of a peptide, polypeptide or protein.

As used herein, a "derivative" of a WNV polypeptide, or a polypeptide that is "derived from" a WNV polypeptide, refers to a polypeptide in which the native form has been purified, modified or altered. Such modifications include, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other modifications, any of which may result in changes in primary, secondary or tertiary structure.

"Substantial binding" refers to an amount of binding or recognizing between molecules in an assay mixture under particular assay conditions. In its broadest aspect, the differentiation between one molecule's incapability of binding or recognizing another molecule and capability of binding or recognizing a third molecule is sufficient to allow a meaningful assay to be conducted under a particular set of assay conditions, which includes the relative concentrations of the molecules. In another aspect, one molecule is substantially incapable of binding or recognizing another molecule in a cross-reactivity sense where the first molecule exhibits a reactivity for a second molecule that is less than 25%, preferably less than 10%, more preferably less than 5% of the reactivity exhibited toward a third molecule under a particular set of assay conditions, which includes the relative concentration of the molecules.

A "biological sample" is any sample from an animal that is expected to contain immunoglobulins. Generally, these samples are whole blood and blood components, but in some circumstances may include saliva, urine, tears, other bodily fluids, tissue extracts or cellular extracts. Test subjects include any animal that may become infected with WNV or are likely to be vaccinated against WNV, and in particular equines. In addition, humans may ultimately be vaccinated against WNV. A sample donor animal refers to a test subject that provides the biological sample.

An "infection," such as in a WNV infection, means that an animal has been exposed to WNV, regardless of whether the animal exhibits clinical symptoms of WNV. A natural infection refers to an exposure that occurs as a result of one of the natural transmission methods for WNV, such as a mosquito bite. An infection does not include an exposure to WNV through vaccination.

A "label" is any molecule that is bound (via covalent or non-covalent means, alone or encapsulated) to another molecule or solid support and that is chosen for specific characteristics that allow detection of the labeled molecule. Generally, labels are comprised of, but are not limited to, the following types: particulate metal and metal-derivatives, radioisotopes, catalytic or enzyme-based reactants, chromogenic substrates and chromophores, fluorescent and chemiluminescent molecules, and phosphors. The utilization of a label produces a signal that may be detected by means such as detection of electromagnetic radiation or direct visualization, and that can optionally be measured.

In one aspect, the invention is directed to a rapid method for screening biological samples for antibodies to WNV. Animals providing biological samples having WNV antibodies have been exposed to WNV antigens, either through a natural infection or through vaccination. Generally, the method includes contacting a biological sample from an animal with a solid phase having immobilized thereon a species specific anti-IgM antibody. This antibody will capture IgM in the biological sample, if any. After washing the solid phase, a synthetic or isolated WNV E protein having a label is added. The labeled protein will bind to any WNV specific IgM captured on the solid phase. The label can be detected by procedures well known in the art of immunoassays.

In one aspect, the invention provides for a method for detecting sample IgM that is a component of an animal's immune response to a WNV vaccine or a natural infection. The method includes obtaining a biological sample from an animal and contacting the sample with a solid phase having immobilized thereon a species specific monoclonal or polyclonal anti-IgM antibody. The solid phase is commonly a microtiter plate or a solid phase matrix of a lateral flow device, but the invention is capable of being practiced in all of formats generally known in the immunoassay arts. Attachment of the antibody to the solid phase can be accomplished by procedures well known to those of skill in the art of antibody immobilization.

The capture and detection of sample IgM that is an animal's immune response to a natural infection or a vaccination can be accomplished in a method referred to herein as a Rapid MAC ELISA. In various aspects, the method includes one or two incubation steps. In the single incubation protocol, the sample and a labeled WNV polypeptide (conjugate) are simultaneously contacted with a solid phase having an immobilized anti-IgM antibody. The sample is incubated, typically for about one hour, before the solid phase is washed to remove unbound reactants. The label is then detected.

In the dual incubation step protocol for the Rapid MAC ELISA, the sample is contacted with the solid phase and incubated for about one hour. Following a washing step to remove the unbound sample components, the solid phase is then contacted with a labeled WNV polypeptide (conjugate) and again incubated, typically for about one hour. Following another washing step, the label can be detected.

In another aspect, the invention provides a method for distinguishing between animals that have been infected with WNV and animals that have been vaccinated with a WNV vaccine or have not been infected. The method exploits the difference between an animal's immune response to a WNV vaccination and an animal's immune response to a WNV infection. For example, animals that have been naturally infected with WNV usually have a higher titer in serum of IgM antibodies to WNV than animals that have been vaccinated. Thus, the method can be optimized so that the assay will be sensitive enough to detect the animal's immune response to a natural infection but will not detect an animal's immune response to a vaccination.

In one aspect, the method is optimized by diluting the sample. Generally, serum samples diluted less than about 1:150 will provide a positive result in the single incubation step Rapid MAC ELISA for animals that have been either infected or vaccinated. A positive result refers to the detection of the label that is bound to the WNV polypeptide. Because of the second incubation step in the dual incubation step Rapid MAC ELISA, the sample can be further substantially diluted and provide similar results. For example, samples for the dual incubation step can be diluted about twice as much, about 1:300, as samples for the single incubation step protocol.

In order to distinguish between animals that have been naturally infected from animals that have been vaccinated, the samples can be diluted to about 1:150 for a single incubation step protocol. Serum samples from vaccinated animals usually do not have a high enough titer of antibodies to WNV to provide a positive result when the sample is diluted about 1:150 or greater. Thus, when the appropriate sample dilution is used, animals that are naturally infected with WNV can be distinguished from animals that have been vaccinated. The dual incubation step protocol can use a higher dilution as describe above.

Because the sensitivity of the method is in part determined by the concentration of the labeled WNV polypeptide (conjugate), the exact dilution at which a sample from a vaccinated animal will no longer provide a positive result depends in part on the working concentration of the conjugate. The appropriate working concentration of the conjugate can be determined based on a maximum signal for a positive control at a specific dilution and a minimal signal for a negative control at that dilution. For the single incubation step protocol, when the controls are diluted about 1:150, the typical range for OD650 for the negative control is about 0.04–0.18 and the typical range for OD650 for the positive control is about 0.46–1.0. For the dual incubation step protocol, when controls are diluted to about 1:300, the typical range for OD650 for the negative control is about 0.035–0.238 and the range for the positive control is about 0.67–1.4.

Once a working concentration of conjugate has been determined, the dilution at which a vaccinated sample will not provide a positive result can be determined by titrating control sera from vaccinated animals in the Rapid MAC ELISA.

Similar to diluting the sample, the method of the invention can be optimized by adjusting the concentration of the working conjugate. For example, a lower sample dilution should not provide a positive result for vaccinated animals when the conjugate concentration is relatively low. Likewise, a higher sample dilution should still provide a positive result for vaccinated animals when the conjugate concentration is relatively high. One of skill in the art could readily adjust the sample dilution and/or the concentration of the conjugate to optimize the method so that the assay will be sensitive enough to detect the animal's immune response to a natural infection but will not detect an animal's immune response to a vaccination.

Additional ways of optimizing the method of the invention include adjusting time and temperature of the incubation periods. In various aspects of the method of the invention, the incubation is at room temperature and the time of the incubation is kept to the shortest period possible. As discussed herein, the method of the invention can be optimized in many ways and one of skill in the art could simultaneously adjust the dilutions, concentrations, temperatures and times used in the method to accomplish a differential detection of serum having antibodies to a WNV infection or vaccination.

The WNV E polypeptide used in the invention contains at least six amino acids, usually at least nine amino acids, and more usually twelve or more amino acids found within the natural WNV E polypeptides and mimitopes and variants thereof. While it is expected that variants of a WNV E polypeptide will have varying binding affinities for WNV antibodies in infected or vaccinated animals, the method of the invention can be optimized to account for the various binding affinities. For example, if polypeptides have a low binding affinity for the sample antibody are used, dilutions less that 1:150 may be used in addition to an increased conjugate concentration. The exact WNV E polypeptide is not a critical feature of the invention as long as the method can be optimized to account for the binding affinity of the polypeptide for the sample WNV antibodies.

For example, WNV variants within the scope of the invention may comprise conservatively substituted sequences, meaning that one or more amino acid residues of the WNV polypeptide are replaced by different residues that do not alter the secondary and/or tertiary structure of the WNV polypeptide. Such substitutions may include the replacement of an amino acid by a residue having similar physicochemical properties, such as, for purposes of example only, substituting one aliphatic residue (Ile, Val, Leu, or Ala) for another, or substitution of basic residues Lys and Arg, acidic residues Glu and Asp, amide residues Gln and Asn, hydroxyl residues Ser and Tyr, or aromatic residues Phe and Tyr. Further information regarding the making of phenotypically silent amino acid exchanges may be found in Bowie et al., *Science* 247:1306–1310 (1990). Other WNV variants that retain substantially the antigenicity of the WNV polypeptides are also contemplated as well as those where the amino acid substitutions are made in the area outside the antibody recognition regions of the protein. Fusion proteins comprising two or more polypeptide sequences of WNV are also within the scope of the invention provided the sequences provide the appropriate antigenicity. Such polypeptides will generally correspond to at least one epitope or mimitope that is characteristic of WNV. By characteristic, it is meant that the epitope or mimitope will allow immunologic detection of antibody directed to WNV in a physiological sample with reasonable assurance. Usually, it will be desirable that the epitope or mimitope, variant or fusion protein be immunologically distinct from (i.e., not cross-reactive with antibodies which recognize) viruses other than WNV.

The WNV polypeptides used as detection reagents may be natural, i.e., isolated from a natural source, or may be synthetic. The natural proteins may be isolated from the whole virus that is obtained as described above by conventional techniques, such as affinity chromatography. Polyclonal or monoclonal antibodies may be used to prepare a suitable affinity column by well-known techniques.

Proteins that are immunologically cross-reactive with a natural WNV protein can be chemically synthesized. For example, polypeptides having fewer than about 100 amino acids, more usually fewer than about 80 amino acids, and typically fewer than about 50 amino acids, may be synthesized by the well-known Merrifield solid-phase synthesis method where amino acids are sequentially added to a growing chain. Merrifield, 1963, *J. Am. Chem. Soc.*, 85:2149–2156). Recombinant proteins can also be used.

These proteins may be produced by expression in cultured cells of recombinant DNA molecules encoding a desired portion of the WNV genome. The portion of the WNV genome may itself be natural or synthetic, with natural genes obtainable from the isolated virus by conventional techniques. Of course, the genome of WNV is RNA, and it will be necessary to transcribe the natural RNA into DNA by conventional techniques employing reverse transcriptase. Polynucleotides may also be synthesized by well-known techniques. For example, short single-stranded DNA fragments may be prepared by the phosphoramidite method described by Beaucage and Carruthers, 1981, Tett. Letters 22:1859–1862. Double-stranded fragments may then be obtained either by synthesizing the complementary strand and then annealing the strands together under appropriate conditions, or by adding the complementary strand using DNA polymerase with an appropriate primer sequence.

The natural or synthetic DNA fragments coding for the desired WNV protein or fragment may be incorporated in a DNA construct capable of introduction to and expression in in vitro cell culture. Usually, the DNA constructs will be suitable for replication in a unicellular host, such as yeast or bacteria. They may also be intended for introduction and integration within the genome of cultured mammalian or other eukaryotic cells. DNA constructs prepared for introduction into bacteria or yeast will include a replication system recognized by the host, the WNV DNA fragment encoding the desired polypeptide product, transcriptional and translational initiation regulatory sequences joined to the 5'-end of the WNV DNA termination regulatory sequences joined to the 3'-end of the fragment. The transcriptional regulatory sequences will include a heterologus promoter that is recognized by the host. Conveniently, a variety of suitable expression vectors are commercially available for a number of hosts. The complete nucleotide sequence for WNV is available from GenBank as accession number AF196835.

To be useful in the detection methods of the present invention, the polypeptides are obtained in a substantially pure form, that is, typically from about 50% w/w or more purity, substantially free of interfering proteins and contaminants. Preferably, the WNV polypeptides are isolated or synthesized in a purity of at least 80% w/w, and more preferably, in at least about 95% w/w purity. Using conventional protein purification techniques, homogeneous polypeptide compositions of at least about 99% w/w purity can be obtained. For example, the proteins may be purified by use of the antibodies described hereinafter using the immunoabsorbant affinity columns described hereinabove.

The method of the invention may be accomplished using immunoassay techniques well known to those of skill in the art, including, but not limited to, using microplates and lateral flow devices. For example, U.S. Pat. No. 5,726,010, which is incorporated herein by reference in its entirety, describes an example of a lateral flow device useful in the present invention. The device of the invention can be used to detect one or more antibodies to WNV polypeptides.

Immobilization of one or more analyte capture reagents, e.g., anti-IgM antibody, onto a device or solid support is performed so that an analyte capture reagent will not be washed away by the sample, diluent and/or wash procedures. One or more analyte capture reagents can be attached to a surface by physical adsorption (i.e., without the use of chemical linkers) or by chemical binding (i.e., with the use of chemical linkers). Chemical binding can generate stronger attachment of specific binding substances on a surface and provide defined orientation and conformation of the surface-bound molecules.

Another embodiment of the invention provides a device that is suitable for a lateral flow assay. For example, a test sample is added to a flow matrix at a first region (a sample application zone). The test sample is carried in a fluid flow path by capillary action to a second region of the flow matrix where a label capable of binding and forming a first complex with an analyte in the test sample. The first complex is carried to a third region of the flow matrix where an anti-IgM is immobilized at a distinct location. A second complex is formed between the immobilized analyte capture reagent and the first complex including the antibody from the sample. For example, a first complex comprising a gold sol particle and a WNV protein bound to a WNV antibody will specifically bind and form a second complex with an immobilized second antibody directed to WNV antibodies. The label that is part of the second complex can be directly visualized.

For example, an anti-IgM antibody can be bound to the solid support in a fluid flow path. The sample is added to the flow path and carried to a region having mobilizable labeled WNV polypeptide that binds to sample IgM. This complex is carried to the region having the bound anti-IgM antibody, thus binding the labeled polypeptide to the flow path. Upon removal of unbound reagents, the label can be detected.

In another aspect, the invention includes one or more labeled specific binding reagents that can be mixed with a test sample prior to application to a device of the invention. In this case it is not necessary to have labeled specific binding reagents deposited and dried on a specific binding reagent pad in the device. A labeled specific binding reagent, whether added to a test sample or pre-deposited on the device, can be for example, a labeled WNV polypeptide or an antibody that specifically binds an antibody for WNV.

Any or all of the above embodiments can be provided as a kit. In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

The device may also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

The following are provided for exemplification purposes only and are not intended to limit the scope of the invention described in broad terms above. All references cited in this disclosure are incorporated herein by reference.

EXAMPLES

Example 1

Recombinant West Nile Virus E-Protein

Recombinant West Nile Virus E-Protein was obtained from L2 Diagnostics, LLC (Haven, Conn.). The apparent molecular weight reported by the vendor and determined by SDS-PAGE is 48 kDa. Protein received from vendor has estimated purity of 95% also based on SDS-PAGE and is stored in 19.6 mM $KH_2PO_4$, 30.4 mM $Na_2HPO_4$, 150 mM NaCl, pH 7.0.

Example 2

Preparation of Microtiter Plates for the Rapid MAC-ELISA

Immulon 2HB 96 well microtiter plates (Dynex Technologies, Inc., Alexandria, Va.) were coated overnight at 4° C. with 1–10 μg/ml of a polyclonal or monoclonal antibody against Horse IgM (Jackson ImmunoResearch Laboratories, Inc., Westgrove, Pa.) in carbonate/bicarbonate buffer, pH 9.5. Following four washes in PBS/TWEEN® 20 reagent, the plates were then blocked with 1% caseine enzyme hydrolysate in 0.5M Tris buffer (pH 7.5) for two hours at room temperature or overnight at 4° C. Following six washes in PBS/TWEEN® 20, the plates were overcoated with 2.5% sucrose in PBS and incubated for at least 1 hour at room temperature. The plates are then aspirated and vacuum dried. Once completely dried, the plates were stored in sealed ziplock or foil bags with dessicant and stored at 4° C. until ready for use.

Example 3

Preparation of rWNV-E:HRP Conjugate

Recombinant WNV-E protein was conjugated to horse radish peroxidase (HRPO) using the sodium meta-periodate method. The conjugation reaction was done at a 1:1 or a 2:1 molar ratio of recombinant WNV-E to HRPO and at an overall protein concentration of 1–3 mg/ml. The reaction was stopped with sodium borohydride and the final conjugate was diluted to 1 mg/ml in an enzyme conjugate diluent containing buffer salts, protein, and preservatives. The working conjugate concentration for each lot of reagents was determined by titration of the stock conjugate when testing a 1:150 dilution of positive and negative control sera on the solid phase. The appropriate working concentration determined based on maximum signal for positive control and minimal signal for negative control. For the single incubation step protocol the typical range for negative control OD650 is 0.04–0.18 and the typical range for positive control OD650 is 0.46–1.0. For the dual incubation step protocol, the typical range for negative control OD 650 is 0.035–0.238 and the typical range for the positive control OD 650 is 0.67–1.4.

Example 4

Single Incubation Step Microtiter Plate Protocol for Rapid MAC ELISA

Once optimal conjugate concentration is determined (in this example about 5 ug/ml), samples and controls are diluted 1:150 in sample diluent containing buffers, salts and preservatives, and added to microtiter plates, 50 ul/well, prepared as in Example 2. The rWNVE:HRPO conjugate is then added to the microtiter plate, 50 ul per well, to same wells containing the diluted sera. Conjugate and sample are then mixed by aspirating and dispensing several times with a multichannel pipet. Conjugate/sample mixture is incubated in the microtiter plate at room temperature for 1 hour. After 8 washes with PBS/TWEEN® 20, 75 ul per well of TMB substrate is added to each well. Substrate is incubated for 5–15 minutes at room temperature. The optical density at 650 nm is read for each well. The positive control and negative control mean OD is determined. A Sample/Negative Control (S/N) ratio is determined for each sample well. S/N ratios greater than or equal to 2.0 are considered positive for IgM and S/N ratios less than 2.0 are considered negative for IgM. Examples of sample data shown in Table 1.

TABLE 1

Rapid MAC-ELISA Single Incubation Step Microtiter Plate Protocol for the Detection of WNV-E Specific IgM in Equine Sera

| Sample | Status[1] | O.D. 650 | S/N |
|---|---|---|---|
| Positive Control | Pos | 0.598 | 7.29 |
| Negative Control | Neg | 0.082 | 1.00 |
| EW1 | Neg | 0.061 | 0.74 |
| EW3 | Neg | 0.046 | 0.56 |
| EW7 | Neg | 0.038 | 0.46 |
| EW8 | Neg | 0.042 | 0.51 |
| EW10 | Neg | 0.045 | 0.55 |
| EW14 | Neg | 0.041 | 0.50 |
| EW21 | Neg | 0.037 | 0.45 |
| EW5 | Pos | 0.427 | 5.21 |
| EW9 | Pos | 0.426 | 5.20 |
| EW12 | Pos | 0.278 | 3.39 |
| EW17 | Pos | 0.340 | 4.15 |
| EW23 | Pos | 0.258 | 3.15 |
| EW25 | Pos | 0.469 | 5.72 |

[1]IgM status based on previous testing with CDC approved reagents.

Example 5

Dual Incubation Step Microtiter Protocol for Rapid MAC ELISA

Once optimal conjugate concentration is determined, samples and controls are diluted 1:300 in sample diluent and added to a microtiter plate at 75 ul/well. Positive and negative controls are run in duplicate. Controls and samples are then incubated for 60 minutes at room temperature. Following 8 washes with PBS-Tween-20, working conjugate (Example 3) is then added to the microtiter plate, 75 ul per well. Conjugate is incubated at room temperature for 1 hour. After 8 washes with PBS/Tween-20, 75 ul per well of TMB Substrate is added to each well. Substrate is incubated for 5–15 minutes at room temperature. The Optical Density at 650 nm is read for each well. The PC and NC mean OD is determined. A Sample/Negative Control (S/N) ratio is determined for each sample well. S/N ratios greater than or equal to 2.0 are considered positive for IgM and S/N ratios less than 2.0 are considered negative for IgM. Examples of sample data generated are shown in Table 2.

TABLE 2

Rapid-MAC-ELISA Dual Incubation Step Microtiter Plate Protocol for the Detection of WNV-E Specific IgM in Equine Sera

| Sample | Status[1] | IgM ELISA O.D.650 | S/N |
|---|---|---|---|
| Positive Control | Pos | 1.138 | 4.35 |
| Negative Control | Neg | 0.262 | 1.00 |
| EW1 | Neg | 0.095 | 0.36 |
| EW3 | Neg | 0.083 | 0.32 |
| EW7 | Neg | 0.082 | 0.31 |
| EW8 | Neg | 0.095 | 0.38 |
| EW10 | Neg | 0.065 | 0.25 |
| EW14 | Neg | 0.066 | 0.25 |
| EW21 | Neg | 0.087 | 0.33 |
| EW5 | Pos | 0.881 | 3.37 |
| EW9 | Pos | 0.774 | 2.96 |
| EW12 | Pos | 0.641 | 2.45 |
| EW17 | Pos | 0.671 | 2.57 |
| EW23 | Pos | 0.720 | 2.75 |
| EW25 | Pos | 0.917 | 3.51 |

[1]IgM status based on previous testing with CDC approved reagents.

Example 6

Detection of IgM Antibodies to WNV-E in Naive Horses Vaccinated with a Commercially Available Vaccine for WNV Seroconversion following vaccination often complicates the diagnosis of WNV in the horse, making it difficult to differentiate vaccination from infection. Presently, only one commercial vaccine is approved for use in the horse and contains formalin-inactivated West Nile virus obtained from Vero cells (Fort Dodge Animal Health). To test the effects of this vaccine on the Rapid MAC-ELISA, blood samples were obtained from eight naïve horses (Silver Valley Veterinary Clinic, Pinehurst, Id.) pre-vaccination (day 0), two weeks after the second in a series of two vaccinations (vaccinations were given on day 0 and day 21, and the samples were taken on day 35) and three weeks after the second vaccination (sample taken on day 42). Serum samples were assayed using the Rapid MAC-ELISA. Results obtained with the single incubation step protocol according to Example 4 are shown in Table 3. Results obtained with the dual incubation step protocol according to Example 5 are shown in Table 4. These results show that the IgM response of vaccinated animals is not strong enough to detect in either the single or dual incubation step protocols of the rapid MAC ELISA at sample dilutions of 1:150 and 1:300, respectively.

TABLE 3

Rapid MAC ELISA Single Incubation Step Protocol

| Horse # | Day 0[1] | Day 35[2] | Day 42[3] |
|---|---|---|---|
| | OD650 | | |
| EWV22 | 0.059 | 0.058 | 0.065 |
| EWV25 | 0.054 | 0.055 | 0.064 |
| EWV26 | 0.047 | 0.050 | 0.058 |
| EWV28 | 0.051 | 0.053 | 0.066 |
| EWV1 | 0.065 | 0.051 | 0.075 |

TABLE 3-continued

Rapid MAC ELISA Single Incubation Step Protocol

| Horse # | Day 0[1] | Day 35[2] | Day 42[3] |
|---|---|---|---|
| EWV16 | 0.055 | 0.062 | 0.075 |
| EWV21 | 0.109 | 0.106 | 0.119 |
| EWV5 | 0.089 | 0.083 | 0.125 |
| | Sample OD/Negative Control | | |
| EWV22 | 0.47 | 0.46 | 0.52 |
| EWV25 | 0.43 | 0.44 | 0.51 |
| EWV26 | 0.37 | 0.40 | 0.46 |
| EWV28 | 0.40 | 0.42 | 0.52 |
| EWV1 | 0.52 | 0.40 | 0.60 |
| EWV16 | 0.44 | 0.49 | 0.60 |
| EWV21 | 0.87 | 0.84 | 0.94 |
| EWV5 | 0.71 | 0.66 | 0.99 |

[1]Naive horses pre-vaccination with formalin killed WNV vaccine (FDAH)
[2]Two weeks after second vaccination
[3]Three weeks after second vaccination

TABLE 4

Rapid MAC ELISA Dual Incubation Step Protocol

| Horse # | Day 0[1] | Day 35[2] | Day 42[3] |
|---|---|---|---|
| | OD 650 | | |
| EWV22 | 0.070 | 0.078 | 0.088 |
| EWV25 | 0.063 | 0.065 | 0.077 |
| EWV26 | 0.057 | 0.059 | 0.079 |
| EWV28 | 0.070 | 0.068 | 0.092 |
| EWV1 | 0.144 | 0.131 | 0.146 |
| EWV16 | 0.080 | 0.087 | 0.102 |
| EWV21 | 0.131 | 0.133 | 0.163 |
| EWV5 | 0.128 | 0.118 | 0.181 |
| | Sample OD/Negative Control | | |
| EWV22 | 0.46 | 0.51 | 0.58 |
| EWV25 | 0.41 | 0.43 | 0.51 |
| EWV26 | 0.38 | 0.39 | 0.52 |
| EWV28 | 0.46 | 0.45 | 0.61 |
| EWV1 | 0.95 | 0.86 | 0.96 |
| EWV16 | 0.53 | 0.57 | 0.67 |
| EWV21 | 0.86 | 0.88 | 1.07 |
| EWV5 | 0.84 | 0.78 | 1.19 |

[1]Naive horses pre-vaccination with formalin killed WNV vaccine (FDAH)
[2]Two weeks after second vaccination
[3]Three weeks after second vaccination Example 7

Discrimination Between Vaccinated and Unvaccinated Horses after WNV Mosquito Challenge With the development of recombinant viruses that express in vivo in the vaccinated animal only the WNV proteins prM, M and E, the rWNVE based MAC-ELISA will be able to detect IgM in vaccinated and unvaccinated horses. Vaccinated horses exhibit a very low or nondetectable IgM titer when exposed to WNV mosquito challenge. Unvaccinated control horses exhibit high IgM titer when exposed to WNV mosquito challenge. Accordingly, serum samples from five control horses and nine horses receiving the recombinant vaccine expressing the WNV prM-E antigens (samples obtained from Merial) were tested prior to vaccination (day 0), three weeks after the first vaccination (sample taken on day 21), two weeks after the second vaccination on day 35 (sample taken on day 49), and two weeks after a mosquito challenge with WNV on day 49 (sample taken on day 63).

None of the vaccinated horses, while all of the unvaccinated control horses, tested positive for IgM following the mosquito challenge with WNV.

TABLE 5

Differentiation of WNV Vaccinated and Unvaccinated Horses After WNV Mosquito Challenge Using the rWNVE Based Rapid MAC-ELISA Single Incubation Step Protocol (OD = 650)
S/N[e] = OD Sample/OD Negative Control

| Horse | Condition | Day 0[a] | S/N | Day 21[b] | S/N | Day 49[c] | S/N | Day 63[d] | S/N |
|---|---|---|---|---|---|---|---|---|---|
| EW 163/91 | Control | 0.053 | 0.42 | 0.049 | 0.39 | 0.046 | 0.37 | 0.363 | 2.88 |
| EW 149/76 | Control | 0.076 | 0.60 | 0.14 | 1.11 | 0.091 | 0.72 | 0.271 | 2.15 |
| EW 159/87 | Control | 0.057 | 0.45 | 0.056 | 0.44 | 0.044 | 0.35 | 0.761 | 6.04 |
| EW 151/78 | Control | 0.056 | 0.44 | 0.041 | 0.33 | 0.069 | 0.55 | 1.337 | 10.61 |
| EW 152/79 | Control | 0.044 | 0.35 | 0.047 | 0.37 | 0.043 | 0.34 | 1.134 | 9.00 |
| EWV 154/81 | Vacc | 0.056 | 0.44 | 0.057 | 0.45 | 0.057 | 0.45 | 0.082 | 0.65 |
| EWV 144/71 | Vacc | 0.051 | 0.40 | 0.069 | 0.55 | 0.049 | 0.39 | 0.063 | 0.50 |
| EWV 148/75 | Vacc | 0.054 | 0.43 | 0.056 | 0.44 | 0.057 | 0.45 | 0.057 | 0.45 |
| EWV 150/77 | Vacc | 0.064 | 0.51 | 0.068 | 0.54 | 0.051 | 0.40 | 0.073 | 0.58 |
| EWV 156/83 | Vacc | 0.055 | 0.44 | 0.062 | 0.49 | 0.059 | 0.47 | 0.077 | 0.61 |
| EWV 157/84 | Vacc | 0.048 | 0.38 | 0.053 | 0.42 | 0.054 | 0.43 | 0.056 | 0.44 |
| EWV 158/86 | Vacc | 0.040 | 0.32 | 0.053 | 0.42 | 0.045 | 0.36 | 0.044 | 0.35 |
| EWV 162/90 | Vacc | 0.053 | 0.42 | 0.064 | 0.51 | 0.048 | 0.38 | 0.133 | 1.06 |
| EWV 153/80 | Vacc | 0.055 | 0.44 | 0.072 | 0.57 | 0.064 | 0.51 | 0.061 | 0.48 |

[a]First vaccination
[b]Three weeks after first vaccination
[c]Two weeks after second vaccination on day 35
[d]Two weeks after WNV challenge on day 49
[e]S/N ≥ 2.0 is positive test result

TABLE 6

Differentiation of WNV Vaccinated and Unvaccinated Horses After WNV Mosquito Challenge Using the rWNVE Based Rapid MAC-ELISA Dual Incubation Step Protocol (OD = 650)
S/N[e] = OD Sample/OD Negative Control

| Horse | Condition | Day 0[a] | S/N | Day 21[b] | S/N | Day 49[c] | S/N | Day 63[d] | S/N |
|---|---|---|---|---|---|---|---|---|---|
| EW 163/91 | Control | 0.056 | 0.37 | 0.058 | 0.38 | 0.053 | 0.35 | 0.464 | 3.05 |
| EW 149/76 | Control | 0.115 | 0.76 | 0.187 | 1.23 | 0.135 | 0.89 | 0.447 | 2.94 |
| EW 159/87 | Control | 0.077 | 0.51 | 0.071 | 0.47 | 0.054 | 0.36 | 1.282 | 8.43 |
| EW 151/78 | Control | 0.066 | 0.43 | 0.049 | 0.32 | 0.096 | 0.63 | 1.683 | 11.07 |
| EW 152/79 | Control | 0.060 | 0.39 | 0.055 | 0.36 | 0.115 | 0.76 | 1.570 | 10.33 |
| EWV 154/81 | Vacc | 0.074 | 0.49 | 0.072 | 0.47 | 0.078 | 0.51 | 0.109 | 0.72 |
| EWV 144/71 | Vacc | 0.068 | 0.45 | 0.073 | 0.48 | 0.062 | 0.41 | 0.116 | 0.76 |
| EWV 148/75 | Vacc | 0.069 | 0.45 | 0.068 | 0.45 | 0.076 | 0.50 | 0.087 | 0.57 |
| EWV 150/77 | Vacc | 0.080 | 0.53 | 0.098 | 0.59 | 0.061 | 0.40 | 0.109 | 0.72 |
| EWV 156/83 | Vacc | 0.075 | 0.49 | 0.094 | 0.62 | 0.089 | 0.59 | 0.181 | 1.19 |
| EWV 157/84 | Vacc | 0.068 | 0.45 | 0.068 | 0.45 | 0.066 | 0.43 | 0.066 | 0.43 |
| EWV 158/86 | Vacc | 0.045 | 0.30 | 0.064 | 0.42 | 0.06 | 0.39 | 0.053 | 0.35 |
| EWV 162/90 | Vacc | 0.066 | 0.43 | 0.076 | 0.50 | 0.058 | 0.38 | 0.218 | 1.43 |
| EWV 153/80 | Vacc | 0.078 | 0.51 | 0.083 | 0.55 | 0.08 | 0.53 | 0.114 | 0.75 |

[a]First vaccination;
[b]Three weeks after first vaccination
[c]Two weeks after second vaccination
[d]Two weeks after WNV challenge
[e]S/N ≥ 2.0 is positive test result This example demonstrates the ability of a recombinant West Nile Virus envelope protein (rWNV-E) to selectively bind antibodies isolated from unvaccinated mosquito challenged horses but not vaccinated mosquito challenged horses. The recombinant WNV vaccine obtained from Merial expresses prM-E antigens.

Although various specific embodiments of the present invention have been described herein, it is to be understood that the invention is not limited to those precise embodiments and that various changes or modifications can be affected therein by one skilled in the art without departing from the scope and spirit of the invention.

What is claimed is:

1. A method for detecting antibodies to West Nile Virus (WNV) in a biological sample, the method comprising:

(a) contacting the biological sample with an immobilized anti-IgM antibody and a synthetic or isolated WNV envelope polypeptide,
   (b) optimizing the method so that the method will detect WNV antibodies in a sample from animals that have been naturally infected but the method will not detect antibodies in a sample from animals that have been vaccinated, and
   (c) detecting whether the polypeptide substantially binds to a WNV antibody in the sample.

2. The method of claim 1 wherein the polypeptide is a recombinant polypeptide.

3. The method of claim 1 wherein the biological sample is from a horse.

4. The method of claim 1 wherein the anti-IgM antibody is anti-horse IgM.

5. The method of claim 1 wherein the polypeptide is conjugated to a label.

6. The method of claim 1 wherein the method is optimized by diluting the sample.

7. The method of claim 1 wherein the method is optimized by adjusting the concentration of the polypeptide.

8. The method of claim 1 wherein the method comprises incubating the sample with a solid phase having the immobilized anti-IgM antibody simultaneously with the polypeptide.

9. The method of claim 1 wherein the method comprises incubating the sample with a solid phase having the immobilized anti-IgM antibody prior to contacting the sample with the polypeptide.

10. The method of claim 9 further comprising a second incubation following the contacting the sample with the polypeptide.

11. A method for detecting a West Nile Virus (WNV) infection in an animal comprising:

(a) contacting the sample with a solid phase having an immobilized anti-IgM antibody;

(b) contacting the sample and the solid phase with a synthetic or isolated WNV envelop polypeptide conjugated to a label;

(c) detecting the label, thereby detecting a WNV infection in the animal;

wherein the method is optimized so that antibodies to WNV that are the animal's immune response to a vaccination cannot be detected.

12. The method of claim 11 wherein the method is optimized by diluting the sample.

13. The method of claim 11 wherein the method is optimized by adjusting the concentration of the labeled WNV polypeptide.

14. The method of claim 11 wherein the method comprises incubating the sample with the solid phase simultaneously with the polypeptide.

15. The method of claim 11 wherein the method comprises incubating the sample with the solid phase prior to contacting the sample with the polypeptide.

16. The method of claim 15 further comprising a second incubation following the contacting the sample with the polypeptide.

* * * * *